(12) United States Patent
Donitzky et al.

(10) Patent No.: US 8,231,221 B2
(45) Date of Patent: Jul. 31, 2012

(54) ARRANGEMENT AND METHOD FOR CARRYING OUT A SURGICAL TREATMENT OF AN EYE

(75) Inventors: Christof Donitzky, Eckental/Eschenau (DE); Peter Riedel, Nürnberg (DE)

(73) Assignee: WAVELIGHT GmbH, Erlangen (DE)

( * ) Notice: Subject to any disclaimer, the term of this patent is extended or adjusted under 35 U.S.C. 154(b) by 84 days.

(21) Appl. No.: 12/894,329

(22) Filed: Sep. 30, 2010

(65) Prior Publication Data

US 2012/0081667 A1    Apr. 5, 2012

(51) Int. Cl.
*A61B 3/10* (2006.01)
(52) U.S. Cl. ......................... 351/221; 351/211
(58) Field of Classification Search .......... 351/200–246; 606/4–6, 107, 166, 167
See application file for complete search history.

(56) References Cited

U.S. PATENT DOCUMENTS

| 5,121,981 | A * | 6/1992 | Waltuck et al. ............... 351/243 |
| 7,905,887 | B2 * | 3/2011 | Moeller et al. ............... 606/107 |
| 2006/0116668 | A1 | 6/2006 | Gray et al. |
| 2009/0318911 | A1 | 12/2009 | Kaushal et al. |
| 2010/0094262 | A1 | 4/2010 | Tripathi et al. |

FOREIGN PATENT DOCUMENTS

| EP | 2184005 A1 | 5/2010 |
| WO | 87/05205 A1 | 9/1987 |

* cited by examiner

*Primary Examiner* — Mohammed Hasan
(74) *Attorney, Agent, or Firm* — Keiko Ichiye

(57) ABSTRACT

An arrangement for carrying out a surgical treatment of an eye includes a diagnostic instrument which is adapted to register eye-structure data. A data processing unit is adapted to generate, on the basis of the eye-structure data registered by the diagnostic instrument, a structural image that contains at least one mapping of a characteristic eye structure and also at least one positional marking arranged relative to the mapping of the characteristic eye structure. An image-data fade-in device is adapted to fade the structural image generated by the data processing unit into an image generated by a surgical microscope during the implementation of a surgical treatment of the eye.

18 Claims, 2 Drawing Sheets

ARRANGEMENT AND METHOD FOR CARRYING OUT A SURGICAL TREATMENT OF AN EYE

The invention relates to an arrangement and a method for carrying out a surgical treatment of an eye.

BACKGROUND OF THE INVENTION

Prior to a surgical intervention in respect of the eye of a patient—for example, the implantation of an intraocular lens—it is customary at the current time to register, by means of a suitable diagnostic instrument, biometric data pertaining to the eye, such as, for example, the depth of the anterior chamber, the thickness of the lens, the length of the eye and/or the refractive power of the cornea. On the basis of the registered refractive power of the cornea, the axial location of an astigmatism can be calculated. Based on the data acquired within the scope of the preliminary examination, markers are placed onto the eye, in particular onto the limbus, which during the intervention serve as a positioning aid for the surgeon, for example when introducing incisions or when inserting the intraocular lens into the eye.

BRIEF SUMMARY OF THE INVENTION

An object underlying the invention is to make available an arrangement and a method for carrying out a surgical treatment of an eye that facilitate the positioning of incisions and/or implants within the eye of the patient.

This object is achieved by an arrangement for carrying out a surgical treatment of an eye. The arrangement includes a diagnostic instrument which is adapted to register eye-structure data. The eye-structure data registered by the diagnostic instrument may be, for example, characteristic image data pertaining to the eye or characteristic image data pertaining to individual regions of the eye. Furthermore, the diagnostic instrument may be adapted to register further biometric data pertaining to the eye, such as, for example, the depth of the anterior chamber, the thickness of the lens, the length of the eye and/or the refractive power of the cornea, on the basis of which the axial length of an astigmatism can be calculated. In the arrangement for carrying out a surgical treatment of an eye, merely one diagnostic instrument for registering the requisite eye-structure data and biometric data may find application. However, if desired or necessary several diagnostic instruments for registering various eye-structure data and biometric data may be provided.

The arrangement according to the invention further includes a data processing unit adapted to generate, on the basis of the eye-structure data registered by the diagnostic instrument, a structural image that contains at least one mapping of a characteristic eye structure and also at least one positional marking arranged relative to the mapping of the characteristic eye structure. The structural image generated by the data processing unit may be stored on a suitable storage medium and/or saved in a suitable database.

The arrangement according to the invention also includes an image-data fade-in device which is adapted to fade the structural image generated by the data processing unit into an image generated by a surgical microscope during the implementation of a surgical treatment of the eye. In principle, it is possible to communicate the image generated by the data processing unit immediately, i.e. without intermediate storage, to the image-data fade-in device. Preferably, however, as elucidated above, an intermediate storage of the structural image generated by the data processing unit is undertaken, so that the structural image of the image-data fade-in device is preferably transmitted from a memory. The transmission of the structural image to the image-data fade-in device may be undertaken via a cable connection or in wireless manner, for example via a WLAN connection. Alternatively, a mobile data-carrier—such as, for example, a USB stick—with the structural image stored thereon can be connected to the image-data fade-in device.

In the course of fading the structural image generated by the data processing unit into the image generated by the surgical microscope an image superimposition is preferably undertaken, i.e. the image generated by the surgical microscope remains visible at least in the regions that are not superimposed by the mapping of the characteristic eye structure or by the positional marking. If desired, the mapping of the characteristic eye structure and/or the positional marking in the structural image generated by the data processing unit may also be represented in partly transparent manner, so that in the course of fading the structural image into the image generated by the surgical microscope the regions of the image generated by the surgical microscope that are superimposed by the mapping of the characteristic eye structure and by the positional marking in the structural image remain partly visible.

By virtue of the fading of the structural image generated by the data processing unit into the image generated by the surgical microscope, in the course of the implementation of a surgical treatment of an eye the arrangement according to the invention provides the surgeon with information about where the positional marking is placed relative to a characteristic eye structure. If the positional marking marks, for example, the location of an incision to be introduced into the eye, the surgeon can consequently infer from the structural image faded into the image generated by the surgical microscope where the incision has to be placed relative to a characteristic eye structure. As a result, the application of markers onto the eye can be dispensed with. Over and above that, the structural image enables a very accurate placement of the positional marking relative to the mapping of the characteristic eye structure. In comparison with a marker that is placed directly onto the eye, the positional marking in the structural image is consequently distinguished by a higher positional accuracy.

The diagnostic instrument of the arrangement for carrying out a surgical treatment of an eye is preferably adapted to register, as the eye-structure data, image data pertaining to blood vessels, iris structures, an iris margin and/or the limbic geometry. In principle, in the arrangement for carrying out a surgical treatment of an eye a diagnostic instrument may find application that is adapted to register selective image data pertaining to blood vessels, iris structures, an iris margin and/or the limbic geometry. Alternatively, however, use may also be made of a diagnostic instrument that is merely adapted to register an overall image, from which corresponding image data pertaining to blood vessels, iris structures, an iris margin and/or the limbic geometry can then be inferred.

The diagnostic instrument preferably includes a light-source that is adapted to accentuate and highlight characteristic eye structures, such as, for example, blood vessels, iris structures, an iris margin and/or the limbic geometry. Alternatively or additionally, the surgical microscope may also include a light-source that is adapted to accentuate and highlight characteristic eye structures, such as, for example, blood vessels, iris structures, an iris margin and/or the limbic geometry. As a result of the irradiation with the light-source, the characteristic eye structures are accentuated and can consequently be registered and recognised more easily and more accurately. The light-source of the diagnostic instrument and/or of the surgical microscope is preferably a source of green light.

The data processing unit of the arrangement according to the invention for carrying out a surgical treatment of an eye may be adapted to generate, on the basis of the eye-structure data registered by the diagnostic instrument, a structural image that contains, as the mapping of a characteristic eye structure, a mapping of a selected blood vessel, of a selected iris structure, of an iris margin and/or of the limbic geometry against a transparent background. The generation of the structural image in the data processing unit can be undertaken with the aid of suitable image-processing software which enables, in addition to the composition of the background, also a suitable composition of the mapping of the characteristic eye structure, for example with regard to the colour scheme, transparency etc.

The data processing unit may furthermore be adapted to generate, on the basis of the eye-structure data registered by the diagnostic instrument, a structural image that contains, by way of positional marking, a marker designed in the form of a point, in the form of a line or in the form of a surface, a grid, and/or an axis indicating the location of an astigmatism. Overall, very much more positional-marking information may consequently be contained in the structural image generated by the data processing unit than can be communicated as a result of the application of markers directly onto the eye.

In principle, the image-data fade-in device can fade the structural image generated by the data processing unit into the image generated by the surgical microscope merely in rigid manner. If he/she desires this, the surgeon can then manually—for example, by rotating the patient and/or by rotating a reclining surface for the patient—cause the mapping of a characteristic eye structure contained in the structural image—such as, for example, of a blood vessel or such like—to coincide with the corresponding 'real' eye structure in the image generated by the surgical microscope. The positional marking in the structural image can then be utilised by the surgeon particularly easily and efficiently.

However, a preferred embodiment of the arrangement according to the invention for carrying out a surgical treatment of an eye includes a positioning device for positioning the faded-in structural image relative to the image generated by the surgical microscope. The positioning device may be integrated into the image-data fade-in device and may include a size-adaptation function, i.e. a zoom function, and/or may enable a displacement and/or rotation of the faded-in structural image relative to the image generated by the surgical microscope. The positioning device may, for example, be manually operable via actuating elements provided on the image-data fade-in device. By virtue of the furnishing of the arrangement according to the invention with a positioning device, the faded-in structural image can be caused to coincide particularly easily and conveniently with the image generated by the surgical microscope, without it being necessary to move the patient for this purpose.

The arrangement according to the invention for carrying out a surgical treatment of an eye may furthermore include a device for recognising a selected eye structure in the image generated by the surgical microscope. Furthermore, the positioning device may be adapted to position the faded-in structural image, depending on the recognised selected eye structure, automatically relative to the image generated by the surgical microscope. For example, the device for recognising a selected eye structure may include an eye-tracker which recognises a pupil in the image of the eye generated by the surgical microscope and also detects the current position of the pupil. The positioning device may then, for example, be adapted to position the faded-in structural image automatically in such a way relative to the image generated by the surgical microscope that a grid contained in the structural image as the positional marking is centred on the midpoint of the pupil.

Furthermore, it is conceivable to employ as a device for recognising a selected eye structure in the image generated by the surgical microscope a device that enables the recognition of a 'real' eye structure in the image generated by the surgical microscope corresponding to the mapping of the characteristic eye structure in the structural image. The positioning device may then be adapted to position the faded-in structural image automatically in such a way relative to the image generated by the surgical microscope that the mapping of the characteristic eye structure in the structural image is caused to coincide with the corresponding 'real' eye structure in the image generated by the surgical microscope.

The device for recognising a selected eye structure in the image generated by the surgical microscope is preferably adapted to work continuously, i.e. to recognise continuously a selected eye structure in the image generated by the surgical microscope. Furthermore, the positioning device is preferably adapted to ensure a continuous tracking of the structural image into the desired position relative to the image generated by the surgical microscope.

A method for carrying out a surgical treatment of an eye includes registering eye-structure data. On the basis of the registered eye-structure data, a structural image is generated that contains at least one mapping of a characteristic eye structure and also at least one positional marking arranged relative to the mapping of the characteristic eye structure. The structural image is faded into an image generated by a surgical microscope during the implementation of a surgical treatment of the eye.

As the eye-structure data, image data pertaining to blood vessels, iris structures, an iris margin and/or the limbic geometry can be registered.

During the registering of the eye-structure data the eye can be irradiated by a light-source that is suitable to accentuate and highlight characteristic eye structures such as, for example, blood vessels, iris structures, an iris margin and/or the limbic geometry. Alternatively or in addition, during the implementation of the surgical treatment of the eye the eye may also be irradiated by a light-source that is adapted to accentuate and highlight characteristic eye structures such as, for example, blood vessels, iris structures, an iris margin and/or the limbic geometry. During the registering of the eye-structure data and/or during the implementation of the surgical treatment of the eye the eye is preferably irradiated with green light by a source of green light.

On the basis of the registered eye-structure data a structural image is preferably generated that contains, as the mapping of the characteristic eye structure, a mapping of a selected blood vessel, of a selected iris structure, of an iris margin and/or of the limbic geometry against a transparent background.

Furthermore, on the basis of the registered eye-structure data a structural image can be generated that contains, as the positional marking, a marker designed in the form of a point, in the form of a line or in the form of a surface, a grid, and/or an axis indicating the location of an astigmatism.

In the method for carrying out a surgical treatment of an eye, the patient and/or a reclining surface for the patient may be moved, in order to position the image generated by the surgical microscope relative to the faded-in structural image, for example in order to cause the mapping of the characteristic eye structure in the structural image to coincide with the 'real' eye structure in the image generated by the surgical microscope. Alternatively, however, the faded-in structural image may also be positioned relative to the image generated by the surgical microscope. As a result, a change of location of the patient during the surgical intervention becomes unnecessary.

Furthermore, a selected eye structure may be recognised in the image generated by the surgical microscope, and the faded-in structural image may be positioned, depending on the recognised selected eye structure, automatically relative to the image generated by the surgical microscope. For example, by means of an eye-tracker the position of a pupil in the image generated by the surgical microscope may be recognised, and the faded-in structural image may be positioned in such a manner relative to the image generated by the surgical microscope that a grid contained in the structural image as the positional marking is centred on the midpoint of the pupil.

Furthermore, it is conceivable to provide the recognition of a 'real' eye structure in the image generated by the surgical microscope corresponding to the mapping of the characteristic eye structure in the structural image, and to position the structural image automatically in such a manner relative to the image generated by the surgical microscope that the mapping of the characteristic eye structure in the structural image is caused to coincide with the corresponding 'real' eye structure in the image generated by the surgical microscope.

If desired, a continuous recognition of a selected eye structure in the image generated by the surgical microscope and a continuous tracking of the position of the faded-in structural image relative to the image generated by the surgical microscope may be undertaken in a manner depending on the recognised selected eye structure.

BRIEF DESCRIPTION OF THE DRAWINGS

The invention will now be elucidated in more detail on the basis of the appended schematic drawings, in which.

DETAILED DESCRIPTION OF PREFERRED EMBODIMENTS

Figure 1:
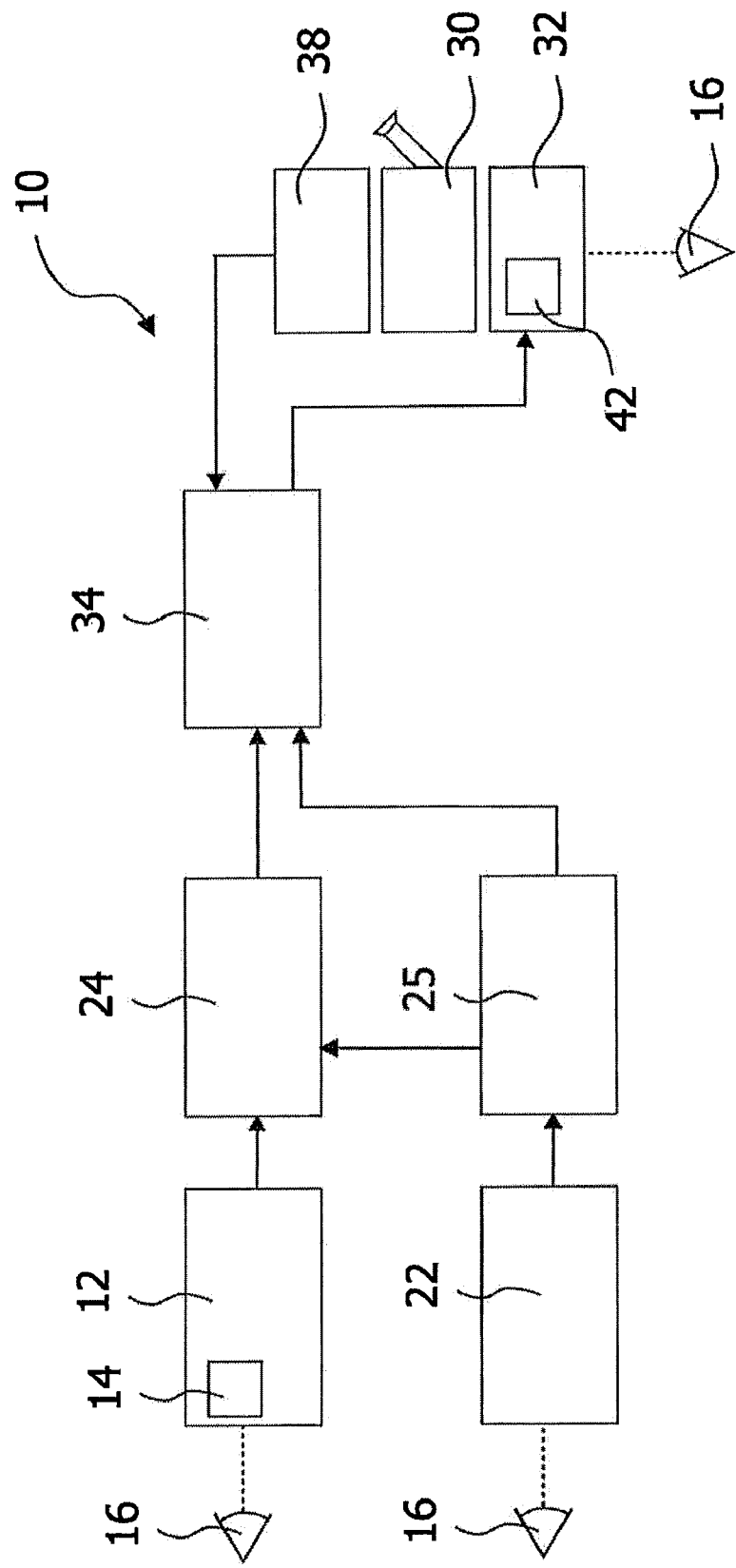
FIG. 1 shows an overall representation of an arrangement for carrying out a surgical treatment of an eye and FIG. 2 shows a schematic representation of an image generated by a surgical microscope during the implementation of a surgical treatment of an eye, into which a structural image generated by a data processing unit has been faded.

FIG. 1 shows an arrangement 10 for carrying out a surgical treatment of an eye 16. The arrangement 10 includes a first diagnostic instrument 12 which is adapted to register eye-structure data. The first diagnostic instrument 12 includes a source of green light 14 with which the eye 16 of a patient can be irradiated with green light within the scope of a preliminary examination. As a result of the irradiation with green light, blood vessels 18 and iris structures 20 as well as the limbic geometry 21 (see FIG. 2) which are present in the eye 16 of the patient are accentuated, so that the first diagnostic instrument 12 can record an image of the eye 16 in which the blood vessels 18 and iris structures 20 as well as the limbic geometry 21 can be readily recognised.

A second diagnostic instrument 22 serves to register further biometric data pertaining to the eye 16, such as, for example, the depth of the anterior chamber, the thickness of the lens, the length of the eye and the refractive power of the cornea, on the basis of which the axial location of an astigmatism can be calculated. In the arrangement 10 represented in FIG. 1 the second diagnostic instrument 22 is formed separately from the first diagnostic instrument 12. If desired, however, the functions of the first and second diagnostic instruments 12, 22 may also be integrated within a single diagnostic instrument.

The image of the eye 16 recorded by the first diagnostic instrument 12 is communicated to a first data processing unit 24. In the exemplary embodiment shown in FIG. 1 the first data processing unit 24 is designed in the form of a personal computer on which image-processing software has been installed. With the aid of the image-processing software, the first data processing unit 24 generates, on the basis of the image of the eye 16 created by the first diagnostic instrument 12, a structural image that contains, as the mappings of characteristic eye structures, mappings of blood vessels 18, iris structures 20 and of the limbic geometry 21 in the eye 16 of the patient.

In similar manner, the further biometric data pertaining to the eye 16 registered by the second diagnostic instrument 22 are communicated to a second data processing unit 25. Just like the first data processing unit 24, the second data processing unit 25 in the exemplary embodiment shown in FIG. 1 is designed in the form of a personal computer, on which suitable software for evaluating the registered biometric data has been installed. The biometric data prepared by the second data processing unit 25 are communicated to the first data processing unit 24.

Taking account of the biometric data communicated to the first data processing unit 24 from the second data processing unit 25, positional markings in the form of a grid 26 and also in the form of an axis 28 indicating the location of an astigmatism (see FIG. 2) are now introduced into the structural image generated by the first data processing unit 24. The structural image exhibits a transparent background and is stored in a database of the first data processing unit 24.

Over and above that, the arrangement 10 includes a surgical microscope 30 which provides an image of the eye 16 during the actual surgical intervention. Furthermore, an image-data fade-in device 32 is present. The image-data fade-in device 32 is controlled by a control device 34, likewise designed in the form of a personal computer, which via a cable connection or a wireless connection has access to the structural image stored in the database of the first data processing unit 24. Over and above that, the control device 34 is supplied by the second data processing unit 25 assigned to the second diagnostic instrument 22 with the biometric data pertaining to the eye 16 registered by the second diagnostic instrument 22. The data communication between the second data processing unit 25 and the control device 34 can likewise be undertaken via a cable connection or a wireless connection.

Figure 2:
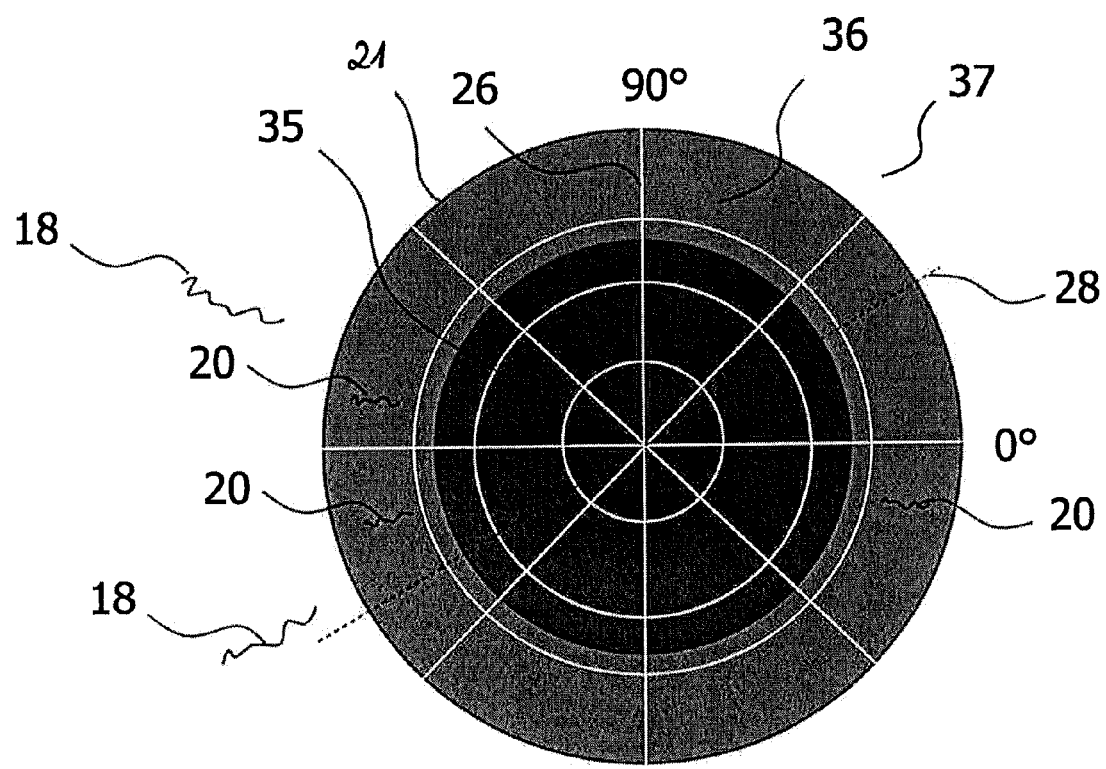

As can be discerned in FIG. 2, the image-data fade-in device 32 is adapted to fade the structural image generated by the first data processing unit 24 into the image of the eye 16 generated by the surgical microscope 30 during the implementation of the actual surgical intervention. In this connection, an image superimposition takes place, whereby the regions of the image generated by the surgical microscope 30 that are not superimposed by the mappings of the blood vessels 18, of the iris structures 20 and of the limbic geometry 21, as well as by the grid 26 and the axis 28, continue to remain visible by virtue of the transparent composition of the background. In particular, the pupil 35, the iris 36 and also the iris-surrounding regions 37 of the eye 16 continue to remain visible.

From the structural image faded into the image generated by the surgical microscope 30 by the image-data fade-in device 32 the surgeon is able to infer where the axis of astigmatism 28 is placed relative to the characteristic eye structures, i.e. the blood vessels 18, the iris structures 20 and the limbic geometry 21. On the basis of this information, the surgeon can, for example, determine in which position and location an intraocular lens is to be implanted into the eye 16.

In the exemplary embodiment shown in FIG. 1 of an arrangement 10, furthermore a device 38 for recognising a selected eye structure in the image generated by the surgical microscope 30 is present. The device 38 includes an eye-tracker which recognises the position of the pupil 35 in the eye 16. Data registered by the device 38 are communicated to the control device 34. Depending on the data registered by the device 38, the structural image faded by the image-data fade-in device 32 into the image generated by the surgical microscope 30 is positioned automatically by means of a positioning device 42 in such a way relative to the image generated by the surgical microscope 30 that the grid 26 contained in the structural image is centred on the midpoint of the pupil 35.

Over and above that, the structural image can be displaced and/or rotated and also zoomed manually via appropriate actuating elements, not illustrated in any detail in FIG. 1, relative to the image generated by the surgical microscope 30. As a result, the mappings contained in the structural image of blood vessels 18, iris structures 20 and of the limbic geometry 21 can be caused to coincide with the corresponding 'real' eye structures in the image generated by the surgical microscope 30, as shown in FIG. 2. The axis 28 contained in the structural image then characterises the 'real' axial location of the astigmatism and consequently provides the surgeon with important information with respect to the positioning of an intraocular lens to be implanted in the eye 16.

In the case of the arrangement 10 shown in FIG. 1 the structural image is displaced, rotated and/or zoomed manually relative to the image generated by the surgical microscope 30, in order to cause the mappings of characteristic eye structures contained in the structural image to coincide with the corresponding 'real' eye structures in the image generated by the surgical microscope 30. Alternatively, the device 38 for recognising a selected eye structure in the image generated by the surgical microscope 30 may also be a device that enables the recognition of a 'real' eye structure in the image generated by the surgical microscope 30 corresponding to the mapping of the characteristic eye structure in the structural image. The positioning device 42 then positions the faded-in structural image automatically in such a way relative to the image generated by the surgical microscope 30 that the mapping of the characteristic eye structure in the structural image is caused to coincide with the corresponding 'real' eye structure in the image generated by the surgical microscope 30.

The invention claimed is:

1. The arrangement for carrying out a surgical treatment of an eye, comprising:
 a diagnostic instrument adapted to register eye-structure data,
 a data processing unit adapted to generate, on the basis of the eye-structure data registered by the diagnostic instrument, a structural image that contains at least one mapping of a characteristic eye structure and also at least one positional marking arranged relative to the mapping of the characteristic eye structure, the structural image comprising, as the mapping of the characteristic eye structure, a mapping of at least one of a blood vessel, an iris structure, an iris margin, and a limbic geometry against a transparent background, and
 an image-data fade-in device which is adapted to fade the structural image generated by the data processing unit into an image generated by a surgical microscope during the implementation of a surgical treatment of the eye.

2. The arrangement according to claim 1, wherein the diagnostic instrument is adapted to register, as the eye-structure data, image data pertaining to at least one of blood vessels, iris structures, an iris margin and the limbic geometry.

3. The arrangement according to claim 1, wherein at least one of the diagnostic instrument and the surgical microscope includes a source of green light.

4. The arrangement according to claim 1, wherein the data processing unit is adapted to generate, on the basis of the eye-structure data registered by the diagnostic instrument, a structural image that contains, as the positional marking, a marker designed in the form of at least one of a point, a line or a surface, a grid, and an axis indicating the location of an astigmatism.

5. The arrangement according to claim 1, further comprising a positioning device for positioning the faded-in structural image relative to the image generated by the surgical microscope.

6. The arrangement according to claim 5, further comprising a device for recognising a selected eye structure in the image generated by the surgical microscope, wherein the positioning device is adapted to position the faded-in structural image, depending on the recognised selected eye structure, automatically relative to the image generated by the surgical microscope.

7. The arrangement according to claim 1, further comprising:
 a positioning device adapted to size-adapt the faded-in structural image relative to the image generated by the surgical microscope.

8. The arrangement according to claim 1, further comprising:
 a positioning device adapted to displace and/or rotate the faded-in structural image relative to the image generated by the surgical microscope.

9. The arrangement according to claim 1, the characteristic eye structure comprising at least two of a blood vessel, an iris structure, an iris margin, and a limbic geometry against a transparent background.

10. A method for carrying out a surgical treatment of an eye, comprising:
 registering eye-structure data;
 generating a structural image on the basis of the registered eye-structure data that contains at least one mapping of a characteristic eye structure and also at least one positional marking arranged relative to the mapping of the characteristic eye structure, the structural image comprising, as the mapping of the characteristic eye structure, a mapping of at least one of a blood vessel, an iris structure, an iris margin, and a limbic geometry against a transparent background; and
 fading the structural image into an image generated by a surgical microscope (30) during the implementation of a surgical treatment of the eye.

11. The method according to claim 10, wherein image data pertaining to at least one of blood vessels, iris structures, an iris margin and the limbic geometry are registered as the eye-structure data.

12. The method according to claim 11, wherein during at least one of the registering of the eye-structure data and the implementation of the surgical treatment of the eye, the eye is irradiated by a source of green light.

13. The method according to claim 10,
wherein on the basis of the registered eye-structure data a structural image is generated that contains, as the positional marking, at least one of a marker designed in the form of a point, line or surface, a grid, and an axis indicating the location of an astigmatism.

14. The method according to claim 1, wherein the faded-in structural image is positioned relative to the image generated by the surgical microscope.

15. The method according to claim 14,
wherein a selected eye structure is recognised in the image generated by the surgical microscope, and the faded-in structural image is positioned, depending on the recognised selected eye structure, automatically relative to the image generated by the surgical microscope.

16. The method according to claim 10, further comprising: size-adapting the faded-in structural image relative to the image generated by the surgical microscope.

17. The method according to claim 10, further comprising: displacing and/or rotating the faded-in structural image relative to the image generated by the surgical microscope.

18. The method according to claim 10, the characteristic eye structure comprising at least two of a blood vessel, an iris structure, an iris margin, and a limbic geometry against a transparent background.

* * * * *